United States Patent
Kumar Luthra et al.

(10) Patent No.: US 9,938,239 B2
(45) Date of Patent: Apr. 10, 2018

(54) METHOD FOR PREPARING SILODOSIN

(71) Applicant: Sandoz AG, Basel (CH)

(72) Inventors: Parven Kumar Luthra, Navi Mumbai (IN); Sachin Bhuta, Navi Mumbai (IN); Chandrakant Abhinay, Navi Mumbai (IN); N. Chaven Dattatraya, Navi Mumbai (IN); D. Metkar Shashikant, Navi Mumbai (IN)

(73) Assignee: Sandoz AG (CH)

( * ) Notice: Subject to any disclaimer, the term of this patent is extended or adjusted under 35 U.S.C. 154(b) by 0 days.

(21) Appl. No.: 14/976,140

(22) Filed: Dec. 21, 2015

(65) Prior Publication Data

US 2016/0176818 A1 Jun. 23, 2016

Related U.S. Application Data

(63) Continuation of application No. 14/352,557, filed as application No. PCT/EP2012/004378 on Oct. 19, 2012, now abandoned.

(60) Provisional application No. 61/549,800, filed on Oct. 21, 2011.

(30) Foreign Application Priority Data

Oct. 21, 2011 (EP) .................................. 11008484

(51) Int. Cl.
*C07D 209/08* (2006.01)
*C07D 209/12* (2006.01)

(52) U.S. Cl.
CPC ......... *C07D 209/08* (2013.01); *C07D 209/12* (2013.01); *Y02P 20/55* (2015.11)

(58) Field of Classification Search
CPC .................................................... C07D 209/08
See application file for complete search history.

(56) References Cited

U.S. PATENT DOCUMENTS 5,387,603 A 2/1995 Kitazawa et al.

FOREIGN PATENT DOCUMENTS

| EP | 0600675 A1 | 8/1994 |
| EP | 1806340 A1 | 11/2007 |
| JP | 2001199956 A | 7/2001 |
| JP | 2002265444 A | 9/2002 |
| JP | 2006188470 A | 7/2006 |
| WO | 2011030356 A2 | 3/2011 |
| WO | 2011124704 A1 | 10/2011 |
| WO | 2012131710 A2 | 10/2012 |

OTHER PUBLICATIONS

International Search Report and Written Opinion for PCT/EP2012-004378, dated Dec. 20, 2012, 11 pages.

*Primary Examiner* — Shawquia Jackson
(74) *Attorney, Agent, or Firm* — Luedeka Neely Group, P.C.

(57) ABSTRACT

The present invention relates to a process for preparing silodosin with high optical purity up to 99.9% enantiomeric excess (e.e.) or above. The process makes use of a method step, in which the enantiomers contained in a racemic mixture of a compound represented by the general formula V: wherein * denotes the asymmetric center, $R^1$ is a protecting group, and $R^2$ is cyano or carbamoyl, are separated.

10 Claims, No Drawings

METHOD FOR PREPARING SILODOSIN

This application is continuation of co-pending application Ser. No. 14/352,557, which is a national phase entry of PCT International application number PCT/EP2012/004378, filed Oct. 19, 2012. This application also claims the benefit of the earlier filing dates of: (1) EP11008484.5, filed Oct. 21, 2011, and (2) U.S. provisional application 61/549,800, filed Oct. 21, 2011.

The present invention relates to a process for preparing silodosin with high optical purity.

Silodosin is commercially available under the tradenames RAPAFLO® or UROREC® as a capsule formulation for oral use containing 4 mg or 8 mg of the drug. The capsules are to be taken orally once daily for the treatment of the signs and symptoms of benign prostatic hyperplasia. U.S. Pat. No. 5,387,603 and EP 0 600 675 disclose silodosin as a therapeutic agent for the treatment for dysurea associated with benign prostatic hyperplasia. The molecular structure of silodosin (XXV) is shown below.

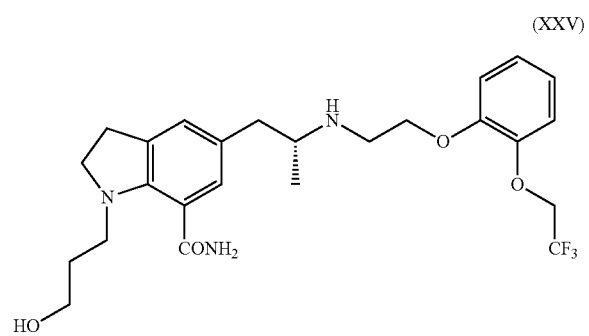 [SMILES: C[C@H](Cc1cc2c(c(C(N)=O)c1)N(CCCO)CC2)NCCOc1ccccc1OCC(F)(F)F]

(XXV)

The synthesis of silodosin is relatively complex and requires a sequence of multiple steps. A key intermediate compound in the synthesis of silodosin is the optically active amine compound represented by the general formula R-V:

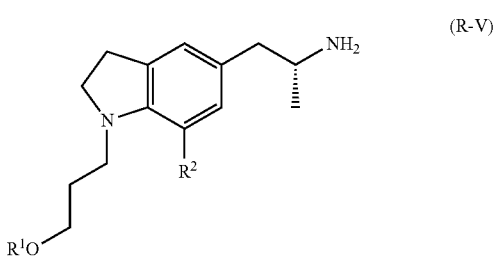

(R-V)

wherein, $R^1$ represents a protecting group and $R^2$ represents a cyano (CN) or carbamoyl ($CONH_2$) group.

The intermediate compound R-V bears the asymmetric carbon atom that imparts the optical activity to silodosin. Therefore, it is important to obtain the compound R-V with high optical purity, because according to the methods reported in the state of the art the optical purity of the compound R-V determines the optical purity of the final product silodosin.

JP 2001-199956 discloses a process for the preparation of a compound of formula R-V, wherein 1-(3-benzoyloxypropyl)-7-cyano-5-(2-oxopropyl)-2,3-dihydroindole or the corresponding 7-carbamoyl derivative is reacted with an optically active amine, namely L-2-phenylglycinol or L-1-phenylethanamine, to afford an imine compound of formula III as depicted in the below scheme 1.

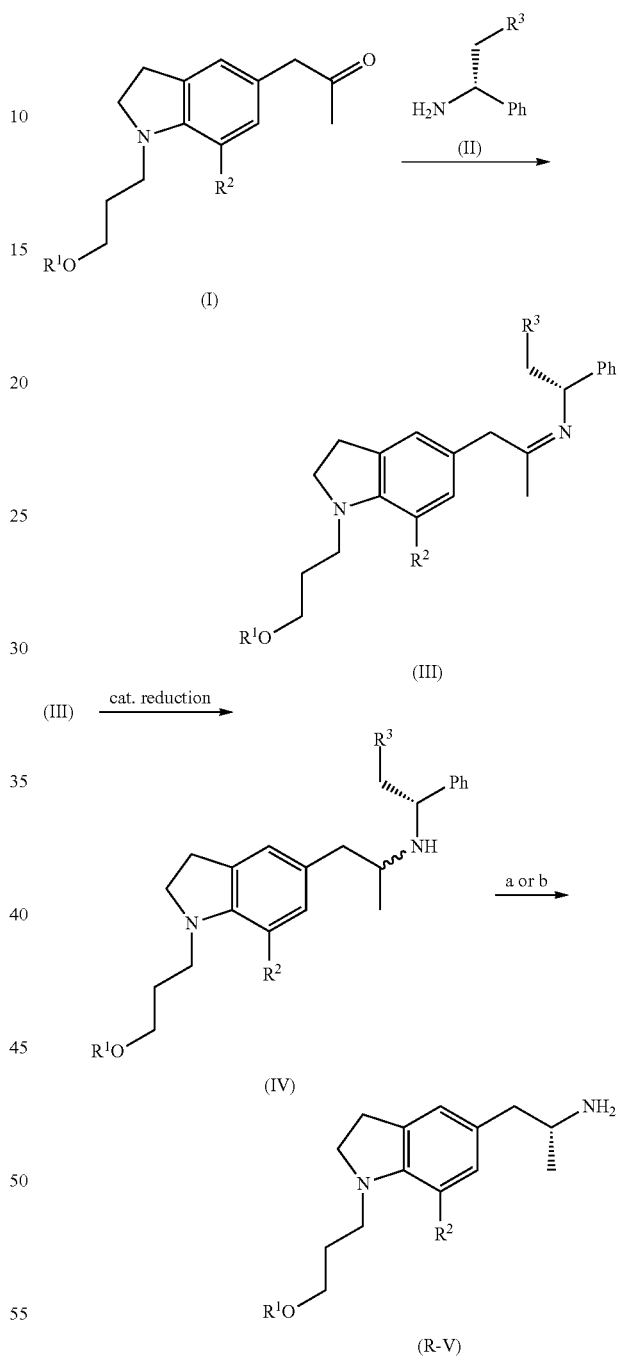

Scheme 1. JP 2001-199956

$R^1$ = COPh; $R^2$ = CN or $CONH_2$; $R^3$ = H or OH
a = 1. cat. deprotection
   2. frational crystallization with L-tartaric acid
b = 1. chromatographic separation
   2. cat. deprotection The optically active imine III is subjected to catalytic hydrogenation using platinum(IV) oxide as a catalyst affording the diastereomers IV in a ratio of 3.8:1. The chiral auxiliary II is subsequently removed by catalytic hydrogenation using 10% palladium on carbon, i.e. under the typical conditions which lead to the cleavage and removal of benzylic protecting groups from nitrogen or oxygen atoms. The catalytic deprotection reaction affords the desired intermediate compound R-V with an optical purity corresponding to the ratio of the diasteromers obtained in the previous step, i.e. the ratio of compound R-V to S-V is approximately 3.8:1, which corresponds to an optical purity of approximately 58.3% enantiomeric excess (e.e.).

In order to increase the optical purity of the intermediate R-V JP 2001-199956 suggests to conduct a fractional crystallization of the desired enantiomer with L-tartaric acid. After a series of fractional crystallizations the compound R-V is obtained with an optical purity of 97.6% enantiomeric excess. Alternatively, the diastereomers of the compound of formula IV are separated using chromatographic techniques as column chromatography on silicagel. The pure diastereomer R-IV affords the desired enantiomer R-V with an optical purity of 100% e.e. after removal of the chiral auxiliary II with hydrogen using 10% palladium on carbon as catalyst.

Another approach for the synthesis of the key intermediate compound R-V is reported in JP 2002-265444. The route of synthesis disclosed in said document is depicted in the below scheme 2.

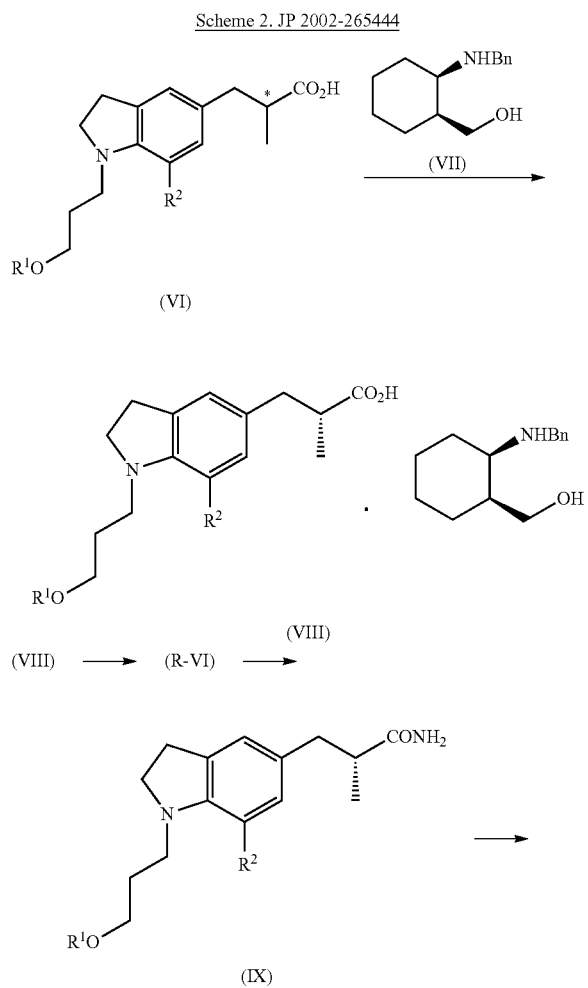

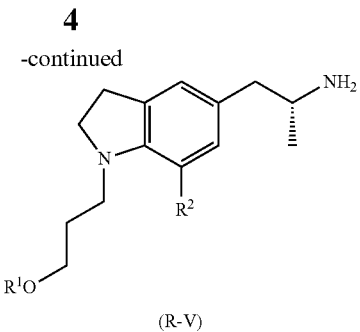

$R^1 = CH_2Ph (Bn); R^2 = CN$

The process involves the reaction of an enantiomeric mixture of the compound of formula VI with (1S,2R)-2-benzylaminocyclohexane methanol (VII) to obtain a diastereomeric mixture containing the salt VIII. After a series of crystallizations the diastereomer VIII was obtained with an optical purity of 92.8% diastereomeric excess (d.e.). Subsequently, the salt VIII was treated with an acidic aqueous solution to release the acid R-VI from the salt. After extraction from the aqueous solution with ethyl acetate the acid R-VI is converted into its amide IX. The compound IX is finally subjected to a Hofmann type rearrangement reaction to obtain the desired intermediate compound R-V.

WO 2011/030356 discloses a process for the preparation of the intermediate compound R-V, which avoids the resolution of the enantiomers of specific intermediate compounds using chiral auxiliaries or optically active bases. The route of synthesis described in WO 2011/030356 starts from L-alanine (X), which is a naturally occurring optically active amino acid. The process described in WO 2011/030356 is depicted in the below scheme 3.

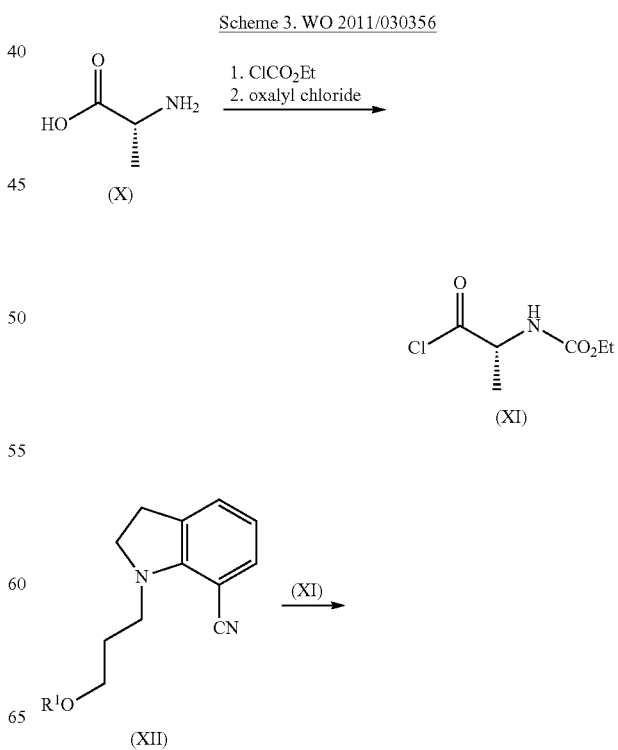

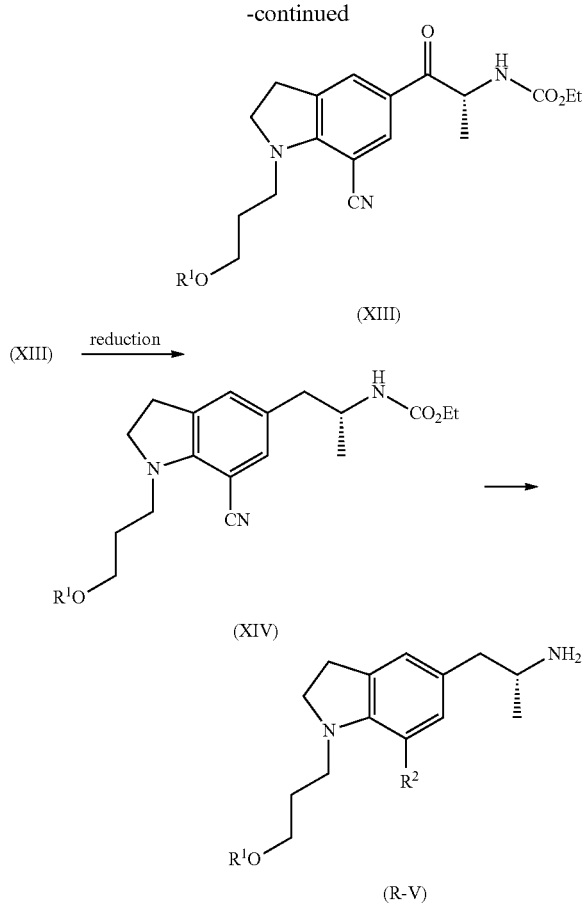

(XIII) → (XIV) → (R-V)

R¹ = trimethylsilyl (TMS), tert-butyl dimethylsilyl (TBDMS), allyl, benzyl, propargyl
R² = CN or CONH₂

The amino acid is protected by the addition of ethyl chloroformate and subsequently activated by the addition of oxalyl chloride to afford R—(N-ethoxycarbonyl)alanine as an acyl chloride (XI). Said acyl chloride is reacted with hydroxy protected 1-(3-hydroxypropyl)-7-cyano-2,3-dihydroindole of formula XII in a Friedel-Crafts acylation reaction, which gives a compound of formula XIII. The oxo group in compound XIII is reduced to afford a compound of formula XIV that is subsequently subjected to a hydrolysis reaction to yield the key intermediate compound R-V.

It is an object of the present invention to provide a process for preparing silodosin or a pharmaceutically acceptable salt thereof, which process affords the drug with high optical purity and with better yield compared to the prior art processes.

This object is solved by the subject matter as defined in the claims.

It was found that it is not necessary to provide the key intermediate compound R-V with high optical purity in order to obtain a silodosin with sufficiently high optical purity, i.e. a silodosin or a pharmaceutically acceptable salt thereof with an optical purity of at least 95% e.e., preferably at least 98% e.e., more preferred at least 99% e.e., and most preferred at least 99.9% e.e. It was surprisingly found that if the key intermediate compound R-V is provided with an optical purity of at least 85% e.e., which affords a crude silodosin with the same optical purity of at least 85% e.e., the crude silodosin can be easily purified by crystallization to obtain the drug with high optical purity. Accordingly, it is not necessary to obtain compound R-V with high optical purity in order to induce a high optical purity in the final product silodosin. It was further found that compound R-V can be obtained with sufficiently high optical purity, i.e. at least 85% e.e., by resolving the enantiomers contained in a racemic mixture of a compound represented by the general formula V:

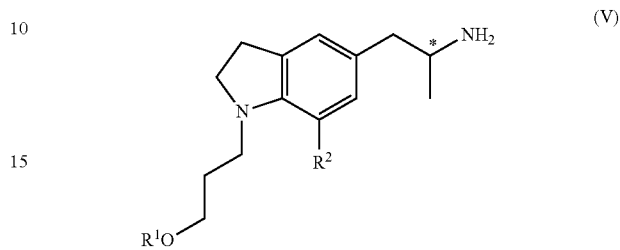

wherein * denotes the asymmetric center, R¹ is the protecting group, and R² is cyano or carbamoyl.

Suitable hydroxy protecting groups are those well known in the art and which may be removed under conventional conditions without disrupting the remainder of the molecule. Particularly suitable hydroxy protecting groups include, for example, triorganosilyl groups, such as triC$_{1-6}$-alkylsilyl, e.g. trimethylsilyl (TMS) and tert-butyl dimethylsilyl (TBDMS), organocarbonyl and organooxycarbonyl groups, such as acetyl, benzoyl (COPh), C$_{1-6}$-alkoxycarbonyl and 4-methoxybenzoyl-oxycarbonyl, unsaturated C$_{2-6}$-alkyl groups, such as allyl and propargyl, and the benzyl group (Bn).

The present invention thus relates to a process for preparing silodosin of formula XXV:

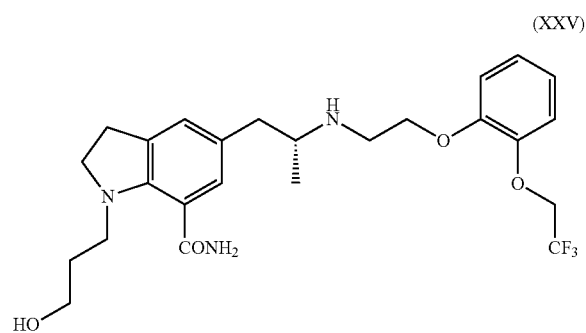

or a pharmaceutically acceptable salt thereof,
which process comprises the method steps of:
a) separating the enantiomers contained in a racemic mixture of a compound represented by the general formula V:

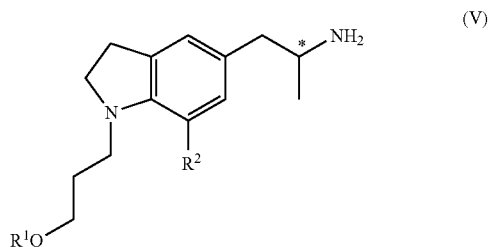

wherein * denotes the asymmetric center,
$R^1$ is a protecting group, and
$R^2$ is cyano or carbamoyl;

b) reacting the R-enantiomer of the compound of formula V (R-V) with a compound represented by formula XXII under reductive animation conditions, or with a compound represented by formula XXIII:

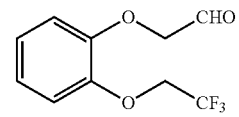
(XXII)

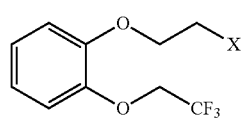
(XXIII)

wherein X represents a leaving group, to obtain a compound represented by the general formula XXIV:

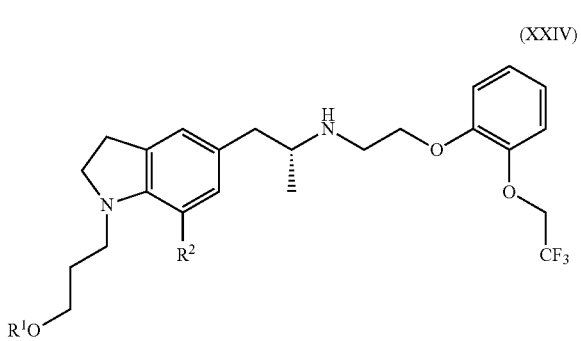
(XXIV)

wherein $R^1$ and $R^2$ have the same meaning as defined above;

c) deprotecting the compound of formula XXIV and, if $R^2$ is cyano, conducting a hydrolysis reaction to afford silodosin; and d) optionally purifying the silodosin obtained in step (c) by crystallization from a solvent.

If in step (a) above the mixture of the compound of formula V is only partially resolved, so that the silodosin or pharmaceutically acceptable salt thereof obtained in method step (c) has an optical purity of between 85% and 95% e.e., preferably between 85% and 98% e.e., the purification of the silodosin obtained in step (c) by crystallization from a solvent is required in order to improve the optical purity up to at least 95% e.e., preferably at least 98% e.e., more preferred at least 99% e.e., and most preferred at least 99.9% e.e.

It was found that the solvent used in method step (d) should contain a carboxylic acid ester, preferably is a carboxylic acid ester. Preferably, the carboxylic acid ester is a C1-6-alkyl acetate, e.g. ethyl acetate, isopropyl acetate, n-butyl acetate, isobutyl acetate or a mixture thereof.

The separation of the compound of formula R-V in step (a) may be conducted by i) dissolving the compound of formula V and an optically active acid in a solvent to obtain a solution of a diastereomeric mixture containing a compound represented by the general formula XXI:

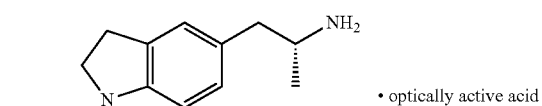
(XXI)

wherein $R^1$ and $R^2$ have the same meaning as defined above, ii) separating the compound of formula XXI from the solution of the diasteriomeric mixture obtained in step (i) by crystallization, iii) dissolving the compound of formula XXI and a base in water, and iv) extracting the compound of formula R-V from the aqueous solution obtained in step (iii) using a water-immiscible solvent.

Preferably, the optically active acid is L-tartaric acid. Most preferred, the compound of formula XXI is the L-tartrate salt of 5-(2R-aminopropyl)-1-(3-benzoyloxypropyl)-7-cyano-2,3-dihydroindole (XXI-tartrate, $R^1$=COPh, $R^2$=CN), which can be obtained from a solution containing acetone and water as solvents with an optical purity of about 85% d.e, by only two crystallizations (above method step (ii)).

The water-immiscible solvent used in the extraction step (iv) preferably contains or is a carboxylic acid ester. The carboxylic acid ester may be a $C_{1-6}$-alkyl acetate, preferably ethyl acetate, isopropyl acetate, n-butyl acetate, isobutyl acetate or a mixture thereof.

The compound V used in the process of the present invention is obtainable by reducing a compound represented by the general formula XX:

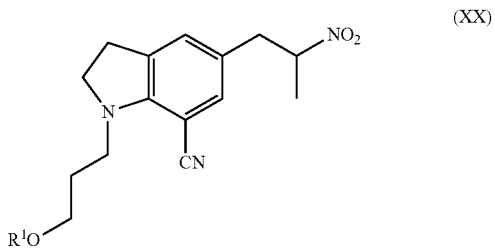
(XX)

wherein $R^1$ has the same meaning as defined above.

The reduction of the compound XX is usually a catalytic hydrogenation using, e.g. platinum on charcoal (e.g. 5% Pt/C) or platinum (IV) oxide as a catalyst.

The synthesis of the compound of formula XX is described in JP 2001-199956. The synthesis of compound XX and its conversion into the compound of V, which is a racemic mixture containing the compounds R-V and S-V in equal amounts, is depicted in the below scheme 4.

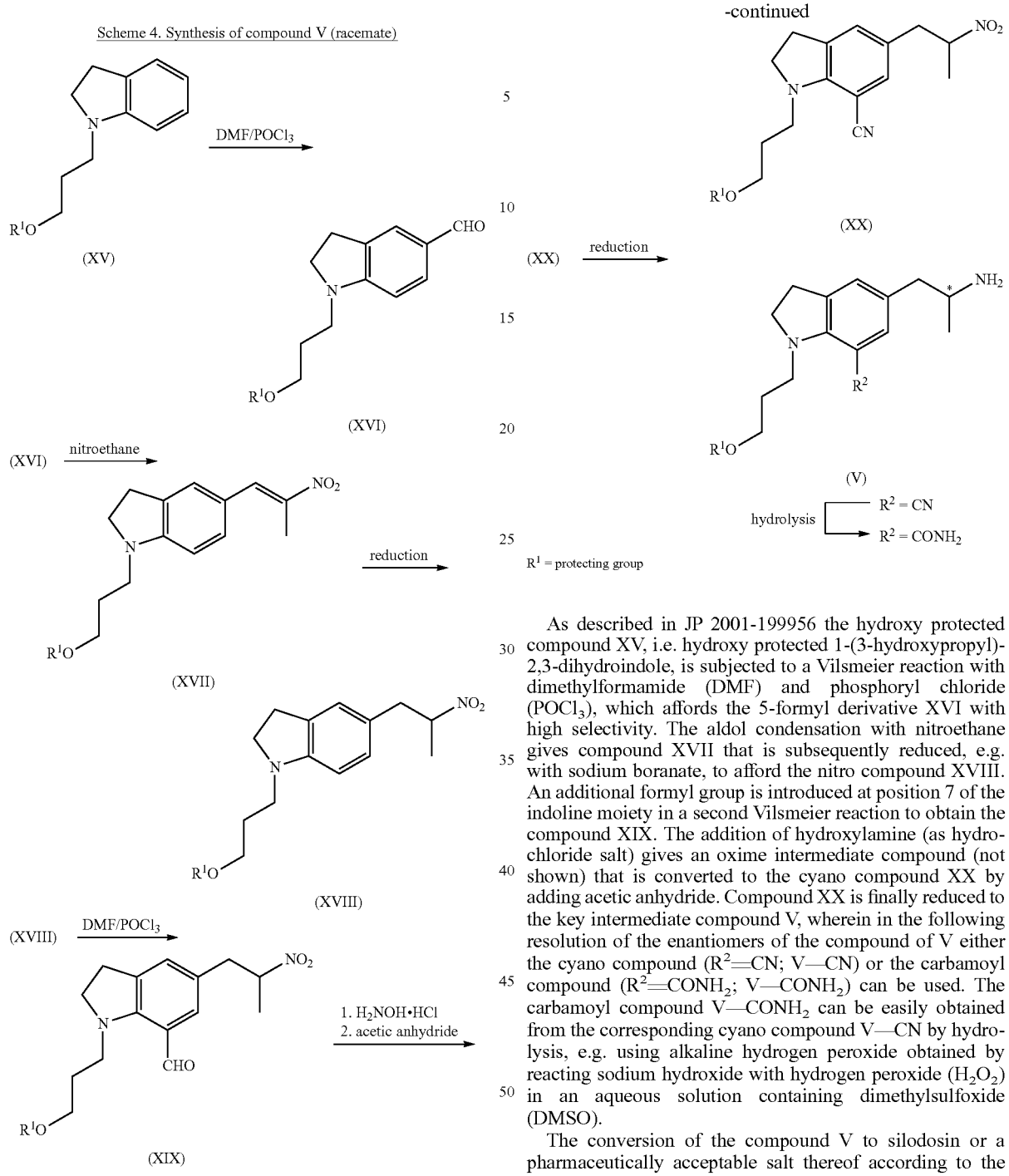

As described in JP 2001-199956 the hydroxy protected compound XV, i.e. hydroxy protected 1-(3-hydroxypropyl)-2,3-dihydroindole, is subjected to a Vilsmeier reaction with dimethylformamide (DMF) and phosphoryl chloride (POCl$_3$), which affords the 5-formyl derivative XVI with high selectivity. The aldol condensation with nitroethane gives compound XVII that is subsequently reduced, e.g. with sodium boranate, to afford the nitro compound XVIII. An additional formyl group is introduced at position 7 of the indoline moiety in a second Vilsmeier reaction to obtain the compound XIX. The addition of hydroxylamine (as hydrochloride salt) gives an oxime intermediate compound (not shown) that is converted to the cyano compound XX by adding acetic anhydride. Compound XX is finally reduced to the key intermediate compound V, wherein in the following resolution of the enantiomers of the compound of V either the cyano compound (R$^2$=CN; V—CN) or the carbamoyl compound (R$^2$=CONH$_2$; V—CONH$_2$) can be used. The carbamoyl compound V—CONH$_2$ can be easily obtained from the corresponding cyano compound V—CN by hydrolysis, e.g. using alkaline hydrogen peroxide obtained by reacting sodium hydroxide with hydrogen peroxide (H$_2$O$_2$) in an aqueous solution containing dimethylsulfoxide (DMSO).

The conversion of the compound V to silodosin or a pharmaceutically acceptable salt thereof according to the present invention is depicted in the below scheme 5.

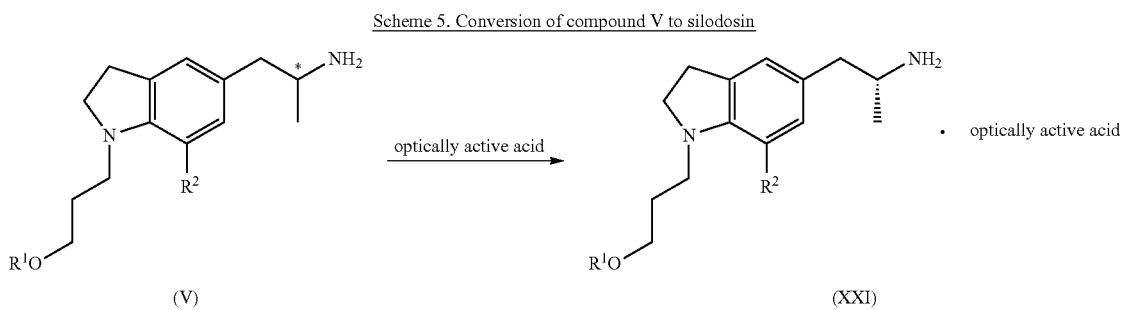

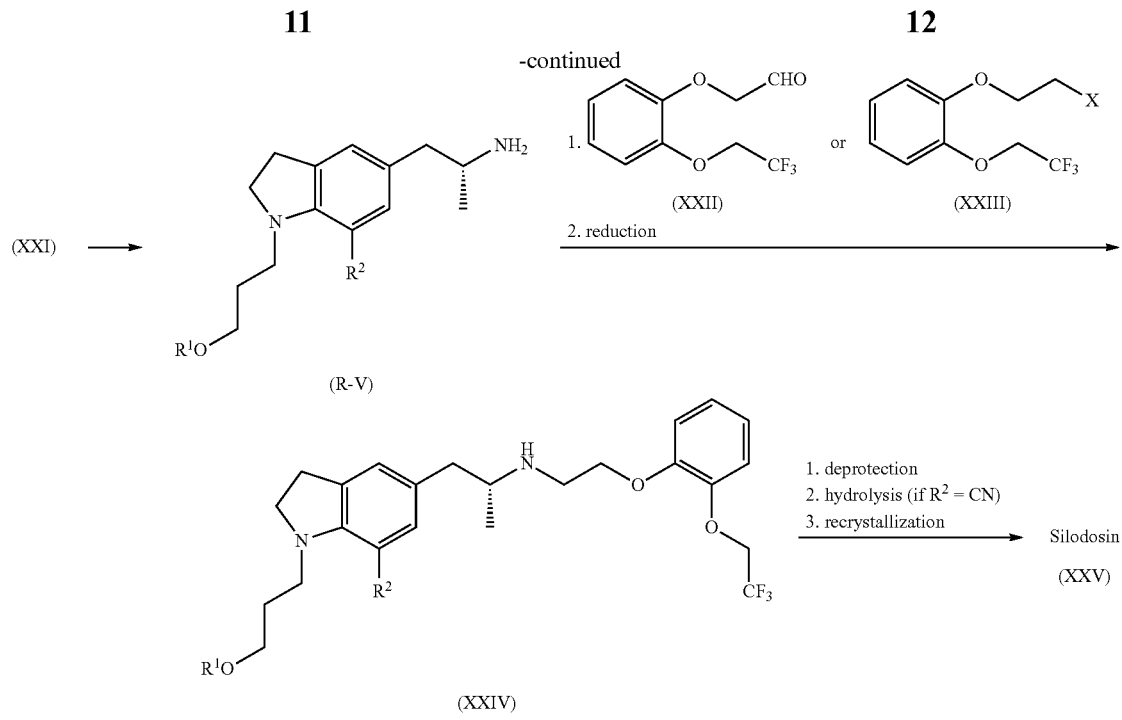

$R^1$ = protecting group
$R^2$ = CN or CONH$_2$
X = leaving group

After separation of the enantiomers contained in the racemic mixture of compound V the enantiomer having the R-configuration, i.e. R-V, is reacted either with [2-(2,2,2-trifluoroethoxy)phenoxy]acetaldehyde (XXII) under reductive amination conditions as described, e.g. in WO 2011/030356, or with a compound of formula XXIII, wherein X is a leaving group as halogen (e.g. Cl, Br or I) or a sulfonyloxy group (e.g. methylsulfonyloxy or toluenesulfonyloxy). The reaction of R-V with compound XXII or XXIII affords the intermediate compound XXIV that is deprotected and optionally hydrolyzed, if $R^2$ is cyano, to yield silodosin (XXV).

The intermediate compound XXIV may contain an impurity derived from the reaction of compound R-V with two molecules of compounds XXII or XXIII, i.e. the corresponding tertiary amine. In order to remove said impurity, the intermediate compound XXIV may be crystallized in form of its oxalic acid addition salt as described in EP 1 806 340 prior to the following deprotection reaction.

Hence, the present invention relates to the use of a racemic mixture of a compound of formula V,

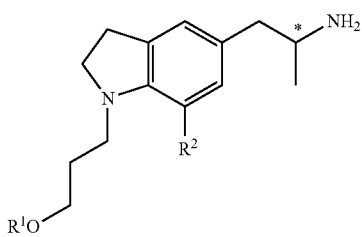

wherein * denotes the asymmetric center,
$R^1$ is a protecting group, and
$R^2$ is cyano or carbamoyl, for the preparation of silodosin or a pharmaceutically acceptable salt thereof.

According to the present invention the racemic mixture of the compound of formula V may be subjected to an enantiomeric resolution procedure to obtain a0 compound of formula R-V:

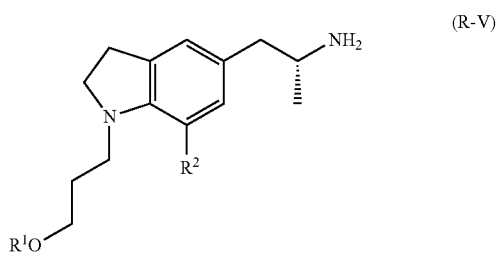

with an optical purity of at least 85% enantiomeric excess (e.e.).

The silodosin or a pharmaceutically acceptable salt thereof having an optical purity of at least 85% e.e., corresponding to the optical purity obtained in the aforementioned resolution procedure, can then be purified by crystallization from a solvent to obtain a silodosin or a pharmaceutically acceptable salt thereof with an optical purity of at least 95% e.e., preferably at least 98% e.e., more preferred at least 99% e.e., most preferred at least 99.9% e.e.

In a preferred embodiment of the present invention, the solvent used for crystallizing silodosin or a pharmaceutically acceptable salt thereof contains a carboxylic acid ester, more preferred is a carboxylic acid ester. Examples of the carboxylic acid ester include $C_{1-6}$-alkyl acetates as ethyl acetate, isopropyl acetate, n-butyl acetate, isobutyl acetate and mixtures thereof, most preferred is ethyl acetate, isopropyl acetate or a mixture thereof.

The following examples are intended to further illustrate the present invention.

EXAMPLES

Example 1.
1-(3-Benzoyloxypropyl)-2,3-dihydroindole (compound XV)

To a solution of benzoic acid (33.0 g) in DMF (65.0 ml), triethylamine (45.0 ml) and 1-bromo-3-chloropropane (21.3 ml) were added in portions over a period of 2 hours.

The reaction mass was stirred over night at room temperature. Triethylamine (19.0 ml) and indoline (i.e. 2,3-dihydroindole; 19.0 ml)) was added to the reaction mass, and the temperature was raised to 100° C. The reaction mixture was stirred at 100° C. for 3 hours. The reaction mass was cooled to room temperature. Water was added, and the product was extracted with ethyl acetate. The organic layer was washed with aqueous sodium bicarbonate solution. The organic solvent was removed, and the residue was dissolved in acetone (90 ml). After addition of hydrochloric acid, 1-(3-benzoyloxypropyl)-2,3-dihydroindole precipitated as hydrochloride salt. The salt was filtered and dried at 60° C.; yield=32.0 g.

Example 2.
1-(3-Benzoyloxypropyl)-5-formyl-2,3-dihydroindole (compound XVI)

DMF (97.0 ml) was cooled to −15° C. and POCl$_3$ (29.0 ml) was added dropwise within 3 h. After completion of the addition, the reaction mixture was stirred for 30 min. and compound XV (41.0 g) was subsequently added. The resulting mixture was stirred for 2 h at room temperature. Thereafter, the reaction mass was hydrolyzed with ice-cold water and neutralized with an aqueous solution of sodium carbonate. The compound XVI was extracted with dichloromethane. Finally the solvent was removed by distillation and crystallized in isopropyl alcohol to obtain 35.0 mg of XVI.

Example 3. 1-(3-Benzoyloxypropyl)-5-(2-nitro-1-propenyl)-2,3-dihydroindole (compound XVII)

A mixture of compound XVI (25.0 g), nitroethane (27.0 ml) and ammonium acetate (8.1 g) was heated to 100° C. and maintained at this temperature for 1.5 h. The reaction mass was stirred over night at room temperature. Water and ethyl acetate were added to the reaction mass. The mixture was cooled to 5° C. and filtered, which afforded 27.0 g of the desired compound XVII.

Example 4. 1-(3-Benzoyloxypropyl)-5-(2-nitropropyl)-2,3-dihydroindole (Compound XVIII)

A solution of compound XVII (16.5 g) in THF (83.0 ml) was cooled to −10° C. and a solution of NaBH$_4$ (2.0 g NaBH$_4$ dissolved in 35 ml of an aqueous 1 N KOH solution) was added dropwise, so that the temperature of the reaction mass did not exceed −5° C. After completion of the addition, the resulting mixture was stirred at room temperature for 2 h. Subsequently, water and ethyl acetate were added, and the pH of the reaction mass was adjusted to 5 by adding 50% acetic acid. The ethyl acetate layer containing compound XVIII was separated and washed with aqueous sodium bicarbonate solution. The solvent was removed to afford compound XVIII.

Example 5. 1-(3-Benzoyloxypropyl)-7-formyl-5-(2-nitropropyl)-2,3-dihydroindole (compound XIX)

POCl$_3$ (21.0 ml) was added to DMF (41.0 ml) cooled at −10° C. within 2 h. After completion of the addition, the reaction mixture was stirred for 30 minutes. Thereafter, a solution of a compound XVIII (40.0 g) in DMF (40.0 ml) was added, so that the temperature in the mixture did not exceed 0° C. After completion of the addition, the reaction mass was stirred at 50° C. for 2 h. The reaction mixture was hydrolyzed with ice-cold water, and the product was extracted with dichloromethane. Removal of the solvent by destillation gave 29.3 g of the desired product XIX.

Example 6. 1-(3-Benzoyloxypropyl)-7-cyano-5-(2-nitropropyl)-2,3-dihydroindole (compound XX)

To a solution of compound XIX (20.0 g) in THF (29.0 ml) hydroxylamine hydrochloride (4.21 g) was added followed by the addition of pyridine (16.0 ml). The reaction mixture was stirred at 50° C. for 2 h, and subsequently acetic anhydride (9.0 ml) was added. The reaction mass was stirred at 80° C. for 2 h. The product was extracted with toluene. The toluene layer was washed with diluted HCl, and the solvent was subsequently removed by distillation to obtain 16.0 g of compound XX.

Example 7. 1-(3-Benzoyloxypropyl)-7-cyano-5-(2-aminopropyl)-2,3-dihydroindole (compound V)

A solution of compound XX (30.0 g) in ethyl acetate (300 ml) was charged to an autoclave and 5% platinum on charcoal (50% wet; 12.0 g) were added. The reaction mass was stirred at 25-30° C. for 8 to 10 h at a hydrogen pressure of 8-10 bar. The resulting suspension was filtered, and the solvent evaporated to afford 25.0 g of the racemic mixture of compound V.

Example 8. 1-(3-Benzoyloxypropyl)-7-cyano-5-(2-aminopropyl)-2,3-dihydroindole L-tartaric acid salt (compound XXI-tartrate)

To a solution of compound V (25.0 g) in acetone (200 ml) an aqueous solution of L-(+)-tartaric acid (10.3 g in 200 ml water) was added. The temperature of the reaction mixture was raised to 65° C. to get a clear solution. After cooling the solution to 25° C. the compound XX-tartrate precipitated. The mixture was stirred at 25° C. for additional 2 h. The salt was filtered and washed with acetone. The wet compound XXI-tartrate was dissolved in a mixture of acetone and water (300 ml; 1:1) at 65° C. The solution was slowly cold to room temperature, the precipitated salt was filtered, and 6.5 g of compound XXI-tartrate with an optical purity of about 85% diastereomeric excess (d.e.) was obtained.

Example 9. 1-(3-Benzoyloxypropyl)-7-cyano-5-(2R-aminopropyl)-2,3-dihydro indole (compound R-V)

The compound XXI-tartrate (10.0 g) was neutralized using an aqueous sodium hydroxide solution. The compound R-V was extracted with ethyl acetate. The ethyl acetate solution containing compound R-V was directly used in the following example 10.

Example 10. 1-(3-Benzoyloxypropyl)-7-cyano-5-(2R-{2-[2-(2,2,2-trifluoroethoxy)phenoxy]ethyl}aminopropyl)-2,3-dihydroindole (compound XXIV)

To the ethyl acetate solution (108 ml) containing the compound R-V obtained in example 9 a solution of [2-(2,2,2-trifluoroethoxy)phenoxy]acetaldehyde (XXII) (10.0 g) in ethyl acetate (80.0 ml) was added. The reaction mixture was stirred for 2 h at room temperature. Subsequently, sodium cyanoborohydride (0.9 g) was added. The reaction mixture was stirred for additional 2 h. The mixture was hydrolyzed with water and acidified. Compound XXIV was extracted with ethyl acetate. The organic solvent was removed by distillation to afford compound XXIV (18.0 g) as an oil.

Example 11. Silodosin (XXV)

A. The compound XXIV (18.0 g) was dissolved in methanol (150 ml) and 5% aqueous sodium hydroxide solution (50 ml). The reaction mixture was stirred at room temperature for 2 h. The deprotected compound XXIV, i.e. a compound of formula XXIV with $R^1$=hydrogen and $R^2$=cyano, was extracted with toluene. Subsequently, a 10% lactic acid solution (25 ml) was added to the toluene phase in order to extract the product in the aqueous phase. The aqueous solution was separated and then basified. The deprotected product was finally extracted with ethyl acetate. Removal of the solvent gives the deprotected compound to XXIV ($R^1$=H and $R^2$=CN; 11.0 g) as an oily mass.

B. A mixture of compound XXIV ($R^1$=H and $R^2$=CN; 10.0 g), DMSO (80 ml) and 5N NaOH solution (9.0 ml) was stirred for 15 min. at room temperature. An aqueous $H_2O_2$ (30%) solution (11.0 ml) was added to the reaction mixture, which was stirred at room temperature for additional 2 h after completion of the addition. Water was added to the reaction mixture, the product was extracted with ethyl acetate, and the solvent was subsequently evaporated to afford 9.0 g crude silodosin.

Example 12. Silodosin (XXV)

10.0 g of crude silodosin (optical purity=85.0% e.e.) was dissolved in ethyl acetate (120 ml) at 55° C. The resulting clear solution was gradually cooled to 25° C. under stirring. The suspension was further cooled to 15° C. and stirred for 2 hours. The precipitated solid was filtered and dried at 50° C. under vacuum to obtain 7.2 g of XXV with an optical purity of 97.5% e.e.

Example 13. Silodosin (XXV)

10.0 g of crude silodosin (optical purity=98.5% e.e.) was dissolved in ethyl acetate (120 ml) at 55° C. The resulting clear solution was gradually cooled to 25° C. under stirring. The suspension was further cooled to 15° C. and stirred for 2 hours. The precipitated solid was filtered and dried at 50° C. under vacuum to obtain 7.2 g of XXV with an optical purity of 99.9% e.e.

Example 14. Silodosin (XXV)

10.0 g of crude silodosin (optical purity=90.0% e.e.) was dissolved in ethyl acetate (120 ml) at 55° C. The resulting clear solution was gradually cooled to 25° C. under stirring. The suspension was further cooled to 15° C. and stirred for 2 hours. The precipitated solid was filtered and dried at 50° C. under vacuum to obtain 7.2 g of XXV with an optical purity of 97.0% e.e.

Example 15. Silodosin (XXV)

10.0 g of crude silodosin (optical purity=92.0% e.e.) was dissolved in isopropyl acetate (160 ml) at 55° C. The resulting clear solution was gradually cooled to 25° C. under stirring. The suspension was further cooled to 15° C. and stirred for 2 hours. The precipitated solid was filtered and dried at 50° C. under vacuum to obtain 8.2 g of XXV with an optical purity of 98.0% e.e.

Example 16. Silodosin (XXV)

10.0 g of crude silodosin (optical purity=98.0% e.e.) was dissolved in isopropyl acetate (160 ml) at 55° C. The resulting clear solution was gradually cooled to 25° C. under stirring. The suspension was further cooled to 15° C. and stirred for 2 hours. The precipitated solid was filtered and dried at 50° C. under vacuum to obtain 8.0 g of XXV with an optical purity of 99.5% e.e.

The invention claimed is:
1. A process for preparing silodosin of formula XXV:

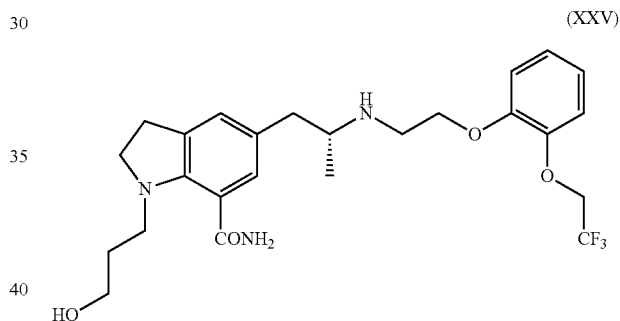

or a pharmaceutically acceptable salt thereof, which process comprises the method steps of:
 a) separating the enantiomers contained in a racemic mixture of a compound represented by formula V:

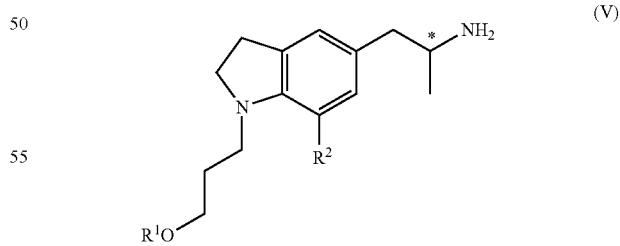

wherein * denotes the asymmetric center,
$R^1$ is a protecting group, and
$R^2$ is cyano or carbamoyl;
 b) reacting the R-enantiomer of the compound of formula V (R-V) with a compound represented by formula XXII under reductive animation conditions, or with a compound represented by formula XXIII:

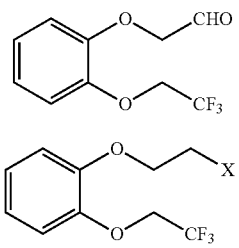

(XXII)

(XXIII)

wherein X represents a leaving group, to obtain a compound represented by formula XXIV:

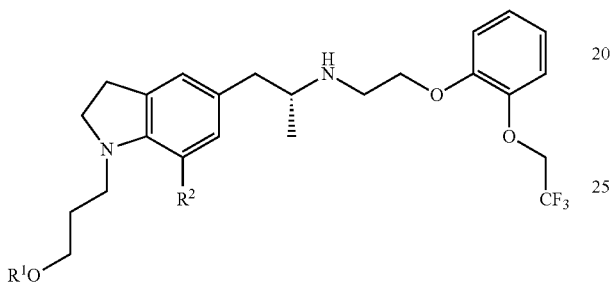

(XXIV)

wherein $R^1$ and $R^2$ have the same meaning as defined above;

c) deprotecting the compound of formula XXIV and, if $R^2$ is cyano, conducting a hydrolysis reaction to afford silodosin; and
d) purifying the silodosin obtained in step (c) by crystallization from a solvent,
wherein the solvent in method step (d) contains a carboxylic acid ester.

2. The process according to claim 1, wherein the carboxylic acid ester is a $C_{1-6}$-alkyl acetate.

3. The process according to claim 1, wherein the separation of the compound of formula R-V in step (a) is conducted by
i) dissolving the compound of formula V and an optically active acid in a solvent to obtain a solution of a diastereomeric mixture containing a compound represented by formula XXI:

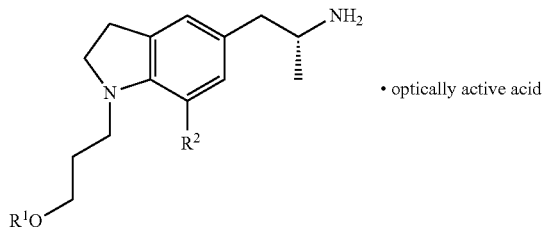

(XXI)

• optically active acid wherein $R^1$ and $R^2$ have the same meaning as defined in claim 1,
ii) separating the compound of formula XXI from the solution of the diasteriomeric mixture obtained in step (i) by crystallization,
iii) dissolving the compound of formula XXI and a base in water, and
iv) extracting the compound of formula R-V from the aqueous solution obtained in step (iii) using a water-immiscible solvent.

4. The process according to claim 3, wherein the optically active acid is L-tartaric acid.

5. The process according to claim 3, wherein the water-immiscible solvent contains a carboxylic acid ester.

6. The process according to claim 5, wherein the carboxylic acid ester is a $C_{1-6}$-alkyl acetate.

7. The process according to claim 1, wherein the compound represented by formula V:

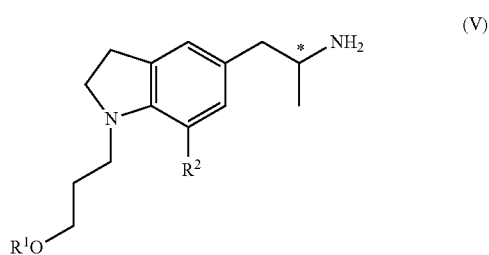

(V)

is prepared by reducing a compound represented by formula XX:

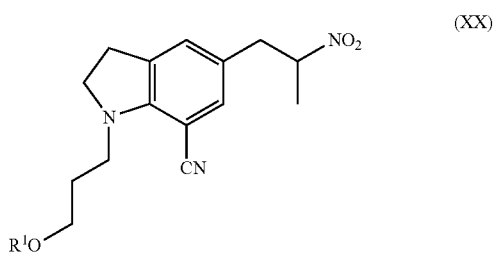

(XX)

wherein $R^1$ has the same meaning as defined in claim 1.

8. The process according to claim 7, wherein the compound XX is subjected to catalytic hydrogenation using platinum on charcoal (e.g. 5% Pt/C) or platinum (IV) oxide as a catalyst.

9. The process according to claim 1, wherein the carboxylic acid ester is selected from the group consisting of ethyl acetate, isopropyl acetate, n-butyl acetate, isobutyl acetate and mixtures thereof.

10. The process according to claim 5, wherein the carboxylic acid ester is selected from the group consisting of ethyl acetate, isopropyl acetate, n-butyl acetate, isobutyl acetate and mixtures thereof.

* * * * *